United States Patent [19]

Lenz et al.

[11] 4,110,325

[45] Aug. 29, 1978

[54] 21-(ACETYLOXY)-3-oxo-24-NORCHOLA-4,20(22)-DIENE-23-NITRILE AND INTERMEDIATES THERETO

[75] Inventors: George R. Lenz, Evanston; John A. Schulz, Waukegan, both of Ill.

[73] Assignee: G. D. Searle & Co., Chicago, Ill.

[21] Appl. No.: 823,372

[22] Filed: Aug. 10, 1977

[51] Int. Cl.$^2$ .......................... C07J 21/00; C07J 9/00
[52] U.S. Cl. ...................... 260/239.55 C; 260/397.47; 260/397.5
[58] Field of Search ......................................................
/Machine Searched Steroids

[56] References Cited

U.S. PATENT DOCUMENTS 3,849,402  11/1974  Kruger .................. 260/239.55 R

OTHER PUBLICATIONS

J. Org. Chem. 35 (1970) p. 1389 by Pettit et al.

Primary Examiner—Elbert L. Roberts
Attorney, Agent, or Firm—John M. Brown

[57] ABSTRACT

Preparation of 21-(acetyloxy)-3-oxo-24-norchola-4,20(22)-diene-23-nitrile; its diuretic, antiulcerogenic, and antiviral utility; and intermediates whereby the preparation can be variously effected are disclosed.

4 Claims, No Drawings

21-(ACETYLOXY)-3-oxo-24-NORCHOLA-4,20(22)-DIENE-23-NITRILE AND INTERMEDIATES THERETO This invention relates to 21-(acetyloxy)-3-oxo-24-norchola-4,20(22)-diene-23-nitrile, intermediates thereto, and processes for the preparation thereof. More particularly, this invention provides a new, useful, and unobvious steroid having the formula

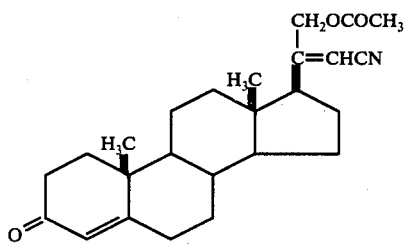

21-(Acetyloxy)-3-oxo-24-norchola-4,20(22)-diene-23-nitrile, the above-enformulated compound, is useful by reason of the valuable biological properties which inhere therein. Thus, for example, the compound is diuretic: When tested via a procedure substantially identical with that described in U.S. Pat. No. 3,926,962 for assaying capacity to reverse the renal electrolyte effects of desoxycorticosterone acetate (DCA), the compound was found to be about 16% as potent as spironolactone subcutaneously, the median effective does being approximately 1.9 mg by this route of administration.

21-(Acetyloxy)-3-oxo-24-norchola-4,20(22)-diene-23-nitrile is also antiulcerogenic, having been found active at a dose of 50 mg (intragastrically) in the standardized test for such utility described in U.S. Pat. No. 3,483,192, and antiviral, the latter utility having been demonstrated in the following standardized test for capacity to inhibit the growth of influenza type B virus (strain MB): Cell cultures of primary monkey kidney maintained in 25-ml plastic flasks each containing test compound in concentrations of 625, 125, 25, 5, or 1 mcgm/ml are prepared in pairs. These flasks, and an identical pair of flasks containing no test compound, are each inoculated with a dose of influenza type B virus (strain MB) previously shown to produce maximum hemadsorption and minimum cytopathogenic effects after a 24-hour incubation. Where the cultures contain test compound, the virus is added 1 hour after addition of the compound to the culture. Following a 24-hour incubation of the cultures, the supernatant fluids are removed and 3.0 ml of a 0.4 percent suspension of guinea pig erythrocytes is added to each flask. The flasks are then incubated at 4° C in a horizontal position for 30 minutes. The flasks are rocked every 10 minutes during the incubation period. After this incubation, the red cell suspension is decanted from each flask, the flasks are washed twice with 3.0 ml of phosphate buffer solution (pH 7.4) to remove unadsorbed red cells, and 3.0 ml of distilled water is then added to lyse the adsorbed cells. The flasks are further incubated at 37° C for 30 minutes in a horizontal position and rocked every 10 minutes. After this incubation, the fluid contents of the pairs of flasks are combined to form an assay unit and maintained at room temperature for 15–30 minutes to allow settling of cellular debris. A pair of control flasks identical with the above except for the absence of test compound and virus inoculation, is run concurrently. The optical density of the resultant hemoglobin solutions is determined via a Beckman spectrophotometer at about 415 millimicrons. A test compound is considered active if, at one of the tested levels, it reduces the optical density by at least 50%, relative to the virus control. 21-(Acetyloxy)-3-oxo-24-norchola-4,20(22)-diene-23-nitrile was found active at 103 mcgm/ml in this test.

In view of the aforesaid diuretic, antiulcerogenic, and antiviral utility of 21-(acetyloxy)-3-oxo-24-norchola-4,20(22)-diene-23-nitrile, intermediates whereby this compound can be prepared are useful also.

A convenient starting material for the preparation of 21-(acetyloxy)-3-oxo-24-norchola-4,20(22)-diene-23-nitrile is DCA, which is converted to the dienol ethyl ether via contact with 1,1'1"-[methylidynetris(oxy)]-trisethane in a mixture of ethanol and 1,4-dioxane containing a catalytic amount of 4-methylbenzenesulfonic acid monohydrate. The dienol ether, in turn, is subjected to prolonged contact, in situ, with the anion formed by mixing diethyl (cyanomethyl)phosphonate with sodium hydride in tetrahydrofuran; and the resultant 21-(acetyloxy)-3-ethoxy-24-norchola-3,5,20(22)-triene-23-nitrile is heated in methanol solution with dilute hydrochloric acid to afford the indicated product.

Alternatively, DCA is converted to the 3-ethylene ketal by vacuum distilling water from a mixture of the DCA with 1,2-ethanediol in the presence of a catalytic amount of 4-methylbenzenesulfonic acid monohydrate; the ketal is condensed with the anion of diethyl (cyanomethyl)phosphonate as outlined above re the dienol ether; and the resultant 21-(acetyloxy)-3-[1,2-ethanediylbis(oxy)]-24-norchola-5,20(22)-diene-23-nitrile is allowed to stand in aqueous acetone containing 4-methylbenzenesulfonic acid monohydrate.

Still another process for preparing 21-(acetyloxy)-3-oxo-24-norchola-4,20(22)-diene-23-nitrile starts with 21-(acetyloxy)pregna-1,4-diene-3,20-dione ($\Delta^1$ DCA), which is condensed with the anion of diethyl (cyanomethyl)phosphonate under conditions previously indicated, affording 21-(acetyl-oxy)-3-oxo-24-norchola-1,4,20(22)-triene-23-nitrile wherein the $\Delta^1$ double bond is reduced by hydrogenation in benzene solution, using chlorotris(triphenylphosphine)rhodium as catalyst.

The following examples describe in detail various methods of preparing 21-(acetyloxy)-3-oxo-24-norchola-4,20(22)-diene-23-nitrile. It will be apparent to those skilled in the art that many modifications, both in materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a solution of 100 parts of DCA in a mixture of 300 parts of 1,4-dioxane, 200 parts of absolute ethanol, and 125 parts of 1,1',1"-[methylidynetris(oxy)]trisethane at approximately 5° is added, with stirring, 6 parts of 4-methylbenzenesulfonic acid monohydrate. Stirring is continued for 15 minutes after the addition is complete, whereupon the reaction mixture is poured into a mixture of 200 parts of pyridine with 10,000 parts of ice-water. The precipitate which forms is 21-(acetyloxy)-3-ethoxypregna-3,5-dien-20-one, which is isolated by filtration and dried in air.

B. The oil is removed from 25 parts of a 50% dispersion of sodium hydride in mineral oil by slurrying the dispersion with a mixture of dimethylbenzenes in a nitrogen atmosphere and then decanting the solvent, whereupon 1000 parts of tetrahydrofuran followed by 176 parts of diethyl (cyanomethyl)phosphonate is added, with stirring under nitrogen, to the sodium hydride. Stirring is continued while exothermy abates, during the addition of a solution of 200 parts of 21-(acetyloxy)-3-ethoxypregna-3,5-dien-20-one in 1000 parts of tetrahydrofuran at this point, and for 16 hours thereafter, whereupon the reaction mixture is poured into 10,000 parts of water. The resultant mixture is acidified to a pH of approximately 4 with 20% hydrochloric acid. The crystalline precipitate which forms is isolated by filtration, washed by slurrying with methanol, and dried in air to give 21-(acetyloxy)-3-ethoxy-24-norchola-3,5,20(22)-triene-23-nitrile melting at 132°-136°.

C. A solution of 1 part of 21-(acetyloxy)-3-ethoxy-24-norchola-3,5,20(22)-triene-23-nitrile in 100 parts of methanol is heated at 50° for ½ hour with 25 parts of 5% hydrochloric acid, then diluted with 500 parts of water. Insoluble solids are filtered out and recrystallized from aqueous methanol to give 21-(acetyloxy)-3-oxo-24-norchola-4,20(22)-diene-23-nitrile melting at 167°-169°. The product has the formula

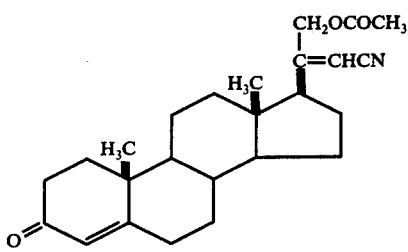

EXAMPLE 2

A. A suspension of 20 parts of DCA in a mixture of 2000 parts of 1,2-ethanediol with 1 part of 4-methylbenzenesulfonic acid monohydrate is concentrated by vacuum distillation at 60°-70° to approximately ¼th its original volume, then cooled to room temperature and thereupon neutralized with 3 parts of pyridine. The resultant mixture is diluted with 1000 parts of distilled water. Insoluble solids are filtered out and dried in air. The material this isolated is 21-(acetyloxy)-3-[1,2-ethanediylbis(oxy)]pregn-5-en-20-one.

B. Substitution of 200 parts of 21-(acetyloxy)-3-[1,2-ethanediylbis(oxy)]pregn-5-en-20-one for the 21-(acetyloxy)-3-ethoxypregna-3,5-dien-20-one called for in Example 1B affords, by the procedure there detailed, 21-(acetyloxy)-3-[1,2-ethanediylbis(oxy)]-24-norchola-5,20(22)-diene-23-nitrile melting in the range 157.5°-163°.

C. To a solution of 10 parts of 21-(acetyloxy)-3-[1,2-ethanediylbis(oxy)]-24-norchola-5,20(22)-diene-23-nitrile in a mixture of 200 parts of 2-propanone with 50 parts of water is added 1 part of 4-methylbenzenesulfonic acid monohydrate. The resultant mixture is allowed to stand at room temperatures overnight, then diluted with 25 volumes of water. The mixture thus obtained is stripped of 2-propanone by vacuum distillation, whereupon insoluble solids are filtered from the distilland and recrystallized from aqueous methanol. The product thus isolated is 21-(acetyloxy)-3-oxo-24-norchola-4,20(22)-diene-23-nitrile.

EXAMPLE 3

A. Substitution of 200 parts of 21-(acetyloxy)pregna-1,4-diene-3,20-dione for the 21-(acetyloxy)-3-ethoxypregna-3,5-diene-20-one called for in Example 1B affords, by the procedure there detailed, 21-(acetyloxy)-3-oxo-24-norchola-1,4,20(22)-triene-23-nitrile melting at 144.5°-148.5°.

B. A solution of 1 part of 21-(acetyloxy)-3-oxo-24-norchola-1,4,20(22)-triene-23-nitrile in 100 parts of benzene is hydrogenated at a pressure of approximately $1.4 \times 10^4$ N m$^{-2}$ and a temperature of around 25° in the presence of 1 part of chlorotris(triphenylphosphine)rhodium until hydrogen uptake indicates that the $\Delta^1$ double bond is reduced, whereupon catalyst is filtered out and the filtrate stripped of solvent by vacuum distillation. The residue is 21-(acetyloxy)-3-oxo-24-norchola-4,20(22)-diene-23-nitrile, which can be further purified by chromatographing on silica gel, using benzene and mixtures thereof with increasing amounts of ethyl acetate as developing solvents.

What is claimed is:

1. 21-(Acetyloxy)-3-oxo-24-norchola-4,20(22)-diene-23-nitrile.
2. 21-(Acetyloxy)-3-ethoxy-24-norchola-3,5,20(22)-triene-23-nitrile
3. 21-(Acetyloxy)-3-[1,2-ethanediylbis(oxy)]-24-norchola-5,20(22)-diene-23-nitrile.
4. 21-(Acetyloxy)-3-oxo-24-norchola-1,4,20(22)-triene-23-nitrile.

* * * * *